US009085656B2

(12) United States Patent
Weikard et al.

(10) Patent No.: US 9,085,656 B2
(45) Date of Patent: *Jul. 21, 2015

(54) LOW VISCOSITY ALLOPHANATES CONTAINING ACTINICALLY CURABLE GROUPS

(75) Inventors: Jan Weikard, Odenthal (DE); Frank Richter, Leverkusen (DE); Christoph Gürtler, Köln (DE); Wolfgang Fischer, Meerbusch (DE); Jörg Schmitz, Köln (DE); Holger Mundstock, Wermelskirchen (DE)

(73) Assignee: Allnex IP S.à.r.l., Luxembourg (LU)

( * ) Notice: Subject to any disclaimer, the term of this patent is extended or adjusted under 35 U.S.C. 154(b) by 1200 days.

This patent is subject to a terminal disclaimer.

(21) Appl. No.: 11/217,727

(22) Filed: Sep. 1, 2005

(65) Prior Publication Data

US 2007/0191570 A1 Aug. 16, 2007

(30) Foreign Application Priority Data

Sep. 9, 2004 (DE) .......................... 10 2004 043 539

(51) Int. Cl.
| C08G 18/79 | (2006.01) |
| C08G 18/67 | (2006.01) |
| C08G 18/18 | (2006.01) |
| C09D 175/00 | (2006.01) |
| C09D 175/14 | (2006.01) |
| C09D 175/16 | (2006.01) |
| C07C 275/60 | (2006.01) |
| C08G 73/00 | (2006.01) |
| C08L 75/00 | (2006.01) |
| C08L 75/16 | (2006.01) |
| C08L 75/14 | (2006.01) |
| C08G 18/78 | (2006.01) |
| C08G 18/81 | (2006.01) |

(52) U.S. Cl.
CPC ............ *C08G 18/798* (2013.01); *C07C 275/60* (2013.01); *C08G 18/1825* (2013.01); *C08G 18/1875* (2013.01); *C08G 18/671* (2013.01); *C08G 18/672* (2013.01); *C08G 18/7837* (2013.01); *C08G 18/8166* (2013.01); *C08G 73/00* (2013.01); *C08L 75/00* (2013.01); *C08L 75/14* (2013.01); *C08L 75/16* (2013.01); *C09D 175/00* (2013.01); *C09D 175/14* (2013.01); *C09D 175/16* (2013.01)

(58) Field of Classification Search
USPC .............. 528/48, 51, 52, 75, 45, 73; 525/127, 525/455
IPC .............. C07C 275/60; C08G 18/1825,18/1875, C08G 18/671, 18/672, 18/798, 73/00, 18/7837; C08L 75/00, 75/14, 75/16; C09D 175/00, C09D 175/14, 175/16
See application file for complete search history.

(56) References Cited

U.S. PATENT DOCUMENTS

| 3,923,743 | A |   | 12/1975 | Quiring et al. |
| 4,160,080 | A |   | 7/1979 | Köenig et al. .................... 528/59 |
| 4,503,226 | A | * | 3/1985 | Tang et al. ...................... 544/193 |
| 5,461,135 | A |   | 10/1995 | Malofsky et al. |
| 5,672,736 | A |   | 9/1997 | Braham et al. |
| 5,719,227 | A | * | 2/1998 | Rosenberry et al. ........... 524/590 |
| 5,739,251 | A |   | 4/1998 | Venham et al. .................. 528/49 |
| 5,777,024 | A |   | 7/1998 | Killilea et al. |
| 5,854,360 | A | * | 12/1998 | Matsunaga et al. ............ 525/452 |
| 5,917,083 | A |   | 6/1999 | König et al. .................... 560/157 |
| 5,951,911 | A |   | 9/1999 | Venham et al. .............. 252/182.2 |
| 6,392,001 | B1 |   | 5/2002 | Mertes et al. .................... 528/59 |
| 6,617,413 | B1 |   | 9/2003 | Bruchmann et al. ............ 528/75 |
| 7,307,135 | B2 |   | 12/2007 | Spyrou |
| 8,202,618 | B2 | * | 6/2012 | Weikard et al. ............. 428/423.1 |
| 2003/0153713 | A1 |   | 8/2003 | Spyrou et al. .................... 528/48 |
| 2005/0003206 | A1 |   | 1/2005 | Spyrou et al. .............. 428/423.1 |
| 2005/0096451 | A1 | * | 5/2005 | Spyrou .......................... 528/44 |
| 2006/0051591 | A1 |   | 3/2006 | Weikard et al. |
| 2006/0052526 | A1 |   | 3/2006 | Weikard et al. |
| 2006/0052527 | A1 |   | 3/2006 | Weikard et al. |

FOREIGN PATENT DOCUMENTS

| CA | 2356685 | * | 7/2000 |
| GB | 994890 |   | 6/1965 |
| JP | 59074112 A |   | 4/1984 |
| JP | 2003048927 A |   | 2/2003 |

OTHER PUBLICATIONS

Proceedings of the International Waterborne, High-Solids, and Powder Coatings Symposium Feb. 21-23, 2001, 28$^{th}$, pp. 405-419, Michaela Gedan-Smolka et al, "New Catalysts for the Low Temperature Curing of Uretdione Powder Coatings".
Angew. Makromol. Chem., 171, (month unavailable) 1989, pp. 21-38, Fleix Schmitt, "Isocyanatfreie, zweikomponentige Polyurethansysteme".
Proceedings of the International Waterborne, High-Solids, and Powder Coatings Symposium Feb. 21-23, 2001, pp. 77-89, K.B. Chandalia et al, "New Non-Isocyanate Curatives for 2K Solvent-Borne Urethane Coatings".

* cited by examiner

*Primary Examiner* — Rabon Sergent
(74) *Attorney, Agent, or Firm* — Drinker Biddle & Reath LLP

(57) ABSTRACT

The present invention relates to a process for preparing radiation-curing binders containing allophanate groups by reacting at temperatures of ≤130° C. A) one or more compounds containing uretdione groups with B) one or more OH-functional compounds which contain groups which react, with polymerization, with ethylenically unsaturated compounds on exposure to actinic radiation, (radiation-curing groups), C) optionally NCO-reactive compounds other than B), in the presence of D) a catalyst containing at least one tetrasubstituted ammonium or phosphonium salt of an aliphatic or cycloaliphatic carboxylic acid, to form allophanate groups by opening the uretdione ring. The present invention also relates to the binders obtained by the process of the invention.

16 Claims, No Drawings

LOW VISCOSITY ALLOPHANATES CONTAINING ACTINICALLY CURABLE GROUPS

CROSS-REFERENCE TO RELATED APPLICATIONS

The present application claims the right of priority under 35 U.S.C. §119 (a)-(d) of German Patent Application No. 10 2004 043 539.1 filed Sep. 9, 2004.

BACKGROUND OF THE INVENTION

1. Field of the Invention

The present invention relates to low viscosity reaction products of alcohols with polyisocyanates, the alcohols containing activated groups which react, with polymerization, with ethylenically unsaturated compounds on exposure to actinic radiation, to a process for preparing them and to their use in coating compositions.

2. Description of Related Art

The curing of coating systems which carry activated double bonds by actinic radiation, such as UV light, IR radiation or electron beams, is known and is established in industry. It is one of the most rapid curing methods in coating technology. Coating compositions based on this principle are thus referred to as radiation- or actinically curing or curable systems.

Because of the environmental and economic requirements imposed on modern coating systems, i.e., that they should use as little organic solvents as possible, or none at all, for adjusting the viscosity, there is a desire to use coatings raw materials which are already of low viscosity. Known for this purpose are polyisocyanates having allophanate groups as described, inter alia, in EP-A 0 682 012.

In industry these substances are prepared by reacting a monohydric or polyhydric alcohol with excess aliphatic and/or cycloaliphatic diisocyanate (cf. GB-A 994 890, EP-A 0 000 194 or EP-A 0 712 840). This is followed by removal of unreacted diisocyanate by means of distillation under reduced pressure. According to DE-A 198 60 041 this procedure can also be carried out with OH-functional compounds having activated double bonds, such as hydroxyalkyl acrylates, although difficulties occur in relation to the preparation of particularly low-monomer products. Since the distillation step has to take place at temperatures up to 135° C., in order to be able to lower the residue isocyanate content sufficiently (<0.5% by weight of residual monomer), it is possible for double bonds to react, with polymerization, under thermal initiation, even during the purification process, meaning that ideal products are no longer obtained.

The preparation of low-monomer-content, allophanate-containing, polyurethane-based, radiation-curing binders is described in EP-A 0 867 457 and U.S. Pat. No. 5,739,251. These binders, however, do not carry activated double bonds but instead carry inert allyl ether groups (structure R—O—$CH_2$—CH=$CH_2$). It is therefore necessary to add reactive diluents (low molecular weight esters of acrylic acid), which introduce the required UV reactivity.

EP-A 0 825 211 describes a process for synthesizing allophanate groups from oxadiazinetriones, although no radiation-curing derivatives having activated double bonds are known. All that is mentioned is the use of maleate- and/or fumarate-containing polyesters; the possibility of radiation curing is not described. U.S. Pat. No. 5,777,024 describes the preparation of low-viscosity radiation-curing allophanates by reacting hydroxy-functional monomers which carry activated double bonds with isocyanate groups of allophanate-modified isocyanurate polyisocyanates. The allophanate-bound radicals are saturated as a result.

The formation of allophanate compounds by ring opening of uretdiones with alcohols is known in principle as a crosslinking mechanism in powder coating materials (cf. Proceedings of the International Waterborne, High-Solids, and Powder Coatings Symposium 2001, 28th, 405-419, and also US-A 2003/0153713). Nevertheless, the reaction temperatures required for this purpose are too high (≥130° C.) for a targeted preparation of radiation-curing monomers based on allophanate with activated double bonds.

Historically the direct reaction of uretdione rings with alcohols to allophanates was first investigated for solventborne, isocyanate-free, 2K [2-component] polyurethane coating materials. Without catalysis this reaction is of no technical importance, due to the low reaction rate (F. Schmitt, Angew. Makromol. Chem. (1989), 171, pp. 21-38). With appropriate catalysts, however, the crosslinking reaction between HDI-based uretdione curatives and polyols is said to begin at 60 to 80° C. (K. B. Chandalia; R. A Englebach; S. L. Goldstein; R. W. Good; S. H. Harris; M. J. Morgan; P. J. Whitman; R. T. Wojcik, Proceedings of the International Waterborne, High-Solids, and Powder Coatings Symposium, (2001), pp. 77-89). The structure of these catalysts has not been published to date. Commercial products prepared by utilizing this reaction are also undisclosed to date.

In summary it may be stated that the preparation of low-viscosity radiation-curing allophanates by ring-opening reaction of alcohols carrying activated double bonds with uretdiones at temperatures ≤130° C. is not disclosed in detail in the prior art.

Surprisingly it has now been found that from the reaction of uretdiones with olefinically unsaturated alcohols, preferably containing activated double bonds, low-viscosity radiation-curing allophanates, which have a low residual monomer content and preferably have viscosities measured at 23° C. of less than 100 000 mPas, can be obtained using ammonium or phosphonium salts of aliphatic or cycloaliphatic carboxylic acids as catalysts even at temperatures ≤130° C.

SUMMARY OF THE INVENTION

The present invention relates to a process for preparing radiation-curing binders containing allophanate groups by reacting at temperatures of ≤130° C.
A) one or more compounds containing uretdione groups with
B) one or more OH-functional compounds which contain groups which react, with polymerization, with ethylenically unsaturated compounds on exposure to actinic radiation, (radiation-curing groups),
C) optionally NCO-reactive compounds other than B),
in the presence
D) a catalyst containing at least one tetrasubstituted ammonium or phosphonium salt of an aliphatic or cycloaliphatic carboxylic acid,
to form allophanate groups by opening the uretdione ring.

The present invention also relates to the binders obtained by the process of the invention.

The present invention further relates to coating compositions containing
a) one or more of the binders obtained in accordance with the invention,
b) optionally one or more polyisocyanates containing free or blocked isocyanate groups, which are free from groups which react, with polymerization, with ethylenically unsaturated compounds on exposure to actinic radiation, c) optionally compounds other than a), which contain groups which react, with polymerization, with ethylenically unsaturated compounds on exposure to actinic radiation, and optionally contain free or blocked NCO groups, d) optionally one or more isocyanate-reactive compounds containing active hydrogen, e) one or more initiators, and f) optionally solvents.

DETAILED DESCRIPTION OF THE INVENTION

Suitable compounds for use as component A) include all organic compounds which contain at least one uretdione group. Preferably they are compounds obtained by the catalytic dimerization of aliphatic, cycloaliphatic and/or araliphatic diisocyanates or polyisocyanates by known methods (cf. J. Prakt. Chem. 1994, 336, page 196-198).

Examples of suitable diisocyanates include 1,4-diisocyanatobutane, 1,6-diisocyanatohexane (HDI), trimethylhexane diisocyanate, 1,3- and 1,4-bis-isocyanatomethylcyclohexane, isophorone diisocyanate (IPDI), 4,4'-diisocyanatodicyclohexylmethanes, 1,3- and 1,4-xylylene diisocyanates (XDI commercial product from Takeda, Japan), diphenylmethane 4,4'-diisocyanate and diphenylmethane 2,4'-diisocyanate (MDI), 2,4- and 2,6-toluene diisocyanate (TDI), or mixtures thereof. 1,6-Diisocyanatohexane is preferred.

Examples of catalysts employed for the dimerization reaction include trialkylphosphines, dimethylaminopyridines and tris(dimethylamino)phosphine. The result of the dimerization reaction depends in known manner on the catalyst used, on the process conditions and on the diisocyanates employed. In particular it is possible for products to be formed which contain on average more than one uretdione group per molecule, the number of uretdione groups being subject to a distribution. Depending upon the catalyst used, the process conditions and the diisocyanates employed, product mixtures are also formed which in addition to uretdiones also contain other structural units, such as isocyanurate and/or iminooxadiazinedione.

Particularly preferred products may be obtained by the catalytic dimerization of HDI and have a free HDI content of less than 0.5% by weight; an NCO content of 17 to 25% by weight, preferably of 21 to 24% by weight; and a viscosity at 23° C. of from 20 to 500 mPas, preferably from 50 to 200 mPas.

The generally NCO-functional compounds obtained by catalytic dimerization are preferably used directly as part of component A), but they can also first be subjected to further reaction and then used as component A). Further reactions include blocking the free NCO groups or further reaction of the NCO groups with NCO-reactive compounds having a functionality of two or more to form iminooxadiazinedione, isocyanurate, urethane, allophanate, biuret urea, oxadiazinetrione, oxazolidinone, acylurea or carbodiimide groups. This results in compounds containing uretdione groups having a higher molecular weight, which, depending on the chosen proportions, may contain NCO groups or may be free from NCO groups.

Suitable blocking agents include alcohols, lactams, oximes, malonates, alkyl acetoacetates, triazoles, phenols, imidazoles, pyrazoles and amines, such as butanone oxime, diisopropylamine, 1,2,4-triazole, dimethyl-1,2,4-triazole, imidazole, diethyl malonate, ethyl acetoacetate, acetone oxime, 3,5-dimethylpyrazole, $\epsilon$-caprolactam, N-tert-butyl-benzylamine, cyclopentanone carboxyethyl ester or mixtures of these blocking agents. The procedure for the blocking of NCO groups is well known and described in Progress in Organic Coatings 1999, 36, 148-172.

NCO-reactive compounds having a functionality of two or more for derivatizing the uretdiones used in A) can be the preceding di- and/or polyisocyanates, and also simple alcohols with a functionality of two or more, such as ethylene glycol, propane-1,2-diol, propane-1,3-diol, diethylene glycol, dipropylene glycol, the isomeric butanediols, neopentyl glycol, hexane-1,6-diol, 2-ethylhexanediol, tripropylene glycol and the alkoxylated derivatives of these alcohols. Preferred dihydric alcohols are hexane-1,6-diol, dipropylene glycol and tripropylene glycol. Suitable trihydric alcohols include glycerol or trimethylolpropane or their alkoxylated derivatives. Tetrahydric alcohols include pentaerythritol or its alkoxylated derivatives.

By actinic radiation is meant electromagnetic, ionizing radiation, especially electron beams, UV radiation and also visible light (Roche Lexikon Medizin, 4th edition; Urban & Fischer Verlag, Munich 1999).

Component B is selected from compounds having groups which react, with polymerization, with ethylenically unsaturated compounds on exposure to actinic radiation (radiation-curing groups). Examples include vinyl, vinyl ether, propenyl, allyl, maleyl, fumaryl, maleimide, dicyclopentadienyl, acrylamide, acrylic and methacrylic groups, preferably vinyl ether, acrylate and/or methacrylate groups, and more preferably acrylate groups.

Examples of suitable hydroxyl-containing compounds B) include 2-hydroxyethyl (meth)acrylate, polyethylene oxide mono(meth)acrylate (e.g. PEA6/PEM6; Laporte Performance Chemicals Ltd., UK), polypropylene oxide mono (meth)acrylate (e.g. PPA6, PPM5S; Laporte Performance Chemicals Ltd., UK), polyalkylene oxide mono(meth)acrylate (e.g. PEM63P, Laporte Performance Chemicals Ltd., UK), poly($\epsilon$-caprolactone) mono(meth)acrylates (e.g. Tone M100® Dow, Schwalbach, DE), 2-hydroxypropyl (meth) acrylate, 4-hydroxybutyl (meth)acrylate, hydroxybutyl vinyl ether, 3-hydroxy-2,2-dimethylpropyl (meth)acrylate, the hydroxy-functional mono-, di- or higher functional acrylates such as glyceryl di(meth)acrylate, trimethylolpropane di(meth)acrylate, pentaerythritol tri(meth)acrylate or dipentaerythritol penta(meth)acrylate, which are obtained by reacting polyhydric, optionally alkoxylated, alcohols such as trimethylolpropane, glycerol, pentaerythritol or dipentaerythritol with (meth)acrylic acid.

Also suitable as component B) are alcohols obtained from the reaction of acids containing double bonds with epoxide compounds optionally containing double bonds, such as the reaction products of (meth)acrylic acid with glycidyl (meth) acrylate or bisphenol A diglycidyl ether. Additionally, it is also possible to use unsaturated alcohols which are obtained from the reaction of optionally unsaturated acid anhydrides with hydroxy compounds and epoxide compounds that optionally contain acrylate groups. Examples include the reaction products of maleic anhydride with 2-hydroxyethyl (meth)acrylate and glycidyl (meth)acrylate.

Preferably, the compounds of component B) correspond to the preceding compounds that have an OH functionality of from 0.9 to 1.1. More preferably, compounds containing primary hydroxyl groups are used in B), such as 2-hydroxyethyl acrylate and 4-hydroxybutyl acrylate.

Besides the OH-functional unsaturated compounds of component B) it is possible in the process of the invention to also use compounds C), which are different from those of B) and contain NCO-reactive groups such as OH, SH or NH. Examples include NH- or SH-functional compounds containing groups which react, with polymerization, with ethylenically unsaturated compounds on exposure to actinic radiation.

Additionally it is possible to incorporate groups having a hydrophilic action, particularly if use from an aqueous medium is envisaged, such as in an aqueous coating material. Groups with a hydrophilic action include ionic groups, which may be either cationic or anionic in nature, and/or nonionic hydrophilic groups. Cationically, anionically or nonionically dispersing compounds are those which contain, for example, sulphonium, ammonium, phosphonium, carboxylate, sulphonate or phosphonate groups or the groups which can be converted into these groups by forming salts (potential ionic groups) or which contain polyether groups and can be incorporated by means of existing isocyanate-reactive groups. Preferred isocyanate-reactive groups are hydroxyl and amino groups.

Examples of suitable ionic compounds or compounds containing potential ionic groups are mono- and dihydroxycarboxylic acids, mono- and diaminocarboxylic acids, mono- and dihydroxysulphonic acids, mono- and diaminosulphonic acids, mono- and dihydroxyphosphonic acids or mono- and diaminophosphonic acids and their salts. Examples include dimethylol propionic acid, dimethylolbutyric acid, hydroxypivalic acid, N-(2-aminoethyl)-β-alanine, 2-(2-aminoethylamino)-ethanesulphonic acid, ethylenediamine-propyl- or butylsulphonic acid, 1,2- or 1,3-propylenediamine-β-ethylsulphonic acid, malic acid, citric acid, glycolic acid, lactic acid, glycine, alanine, taurine, lysine, 3,5-diaminobenzoic acid, an adduct of IPDI and acrylic acid (EP-A 0 916 647, Example 1) and its alkali metal and/or ammonium salts, the adduct of sodium bisulphite with but-2-ene-1,4-diol, polyethersulphonate, the propoxylated adduct of 2-butenediol and $NaHSO_3$ (described for example in DE-A 2 446 440, page 5-9, formula I-III) and also structural units which can be converted into cationic groups, such as N-methyldiethanolamine.

Preferred ionic or potential ionic compounds are those having carboxyl or carboxylate, sulphonate groups and/or ammonium groups. Particularly preferred ionic compounds are those which contain carboxyl and/or sulphonate groups as ionic or potential ionic groups, such as the salts of N-(2-aminoethyl)-β-alanine, 2-(2-aminoethylamino)ethanesulphonic acid, the adduct of IPDI and acrylic acid (EP-A-0 916 647, Example 1) and also dimethylolpropionic acid.

Suitable nonionic hydrophilic compounds include polyoxyalkylene ethers containing at least one hydroxyl or amino group. These polyethers include a fraction of from 30% to 100% by weight of units derived from ethylene oxide.

Suitable compounds include linear polyethers having a functionality of from 1 to 3, and also compounds of formula (I),

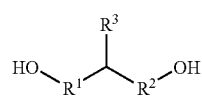

(I)

wherein
$R^1$ and $R^2$ independently of one another are each a divalent aliphatic, cycloaliphatic or aromatic radical having 1 to 18 carbon atoms, which may be interrupted by oxygen and/or nitrogen atoms, and
$R^3$ is an alkoxy-terminated polyethylene oxide radical.

Nonionic hydrophilic compounds also include monohydric polyalkylene oxide polyether alcohols containing on average 5 to 70, preferably 7 to 55, ethylene oxide units per molecule, such as those obtained in known manner by alkoxylating suitable starter molecules (e.g. in Ullmanns Encyclopädie der technischen Chemie, 4th edition, volume 19, Verlag Chemie, Weinheim pp. 31-38).

Examples of suitable starter molecules include saturated monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols, hydroxymethylcyclohexane, 3-ethyl-3-hydroxymethyloxetane, tetrahydrofurfiiryl alcohol, diethylene glycol monoalkyl ethers such as diethylene glycol monobutyl ether, unsaturated alcohols (such as allyl alcohol, 1,1-dimethylallyl alcohol or oleyl alcohol), aromatic alcohols such as phenol, the isomeric cresols or methoxyphenols, araliphatic alcohols (such as benzyl alcohol, anisyl alcohol or cinnamyl alcohol), secondary monoamines (such as dimethylamine, diethylamine, dipropylamine, diisopropylamine, dibutylamine, bis(2-ethylhexyl)amine, N-methyl- and N-ethylcyclohexylamine or dicyclohexylamine) and also heterocyclic secondary amines (such as morpholine, pyrrolidine, piperidine or 1H-pyrazole). Preferred starter molecules are saturated monoalcohols. Particular preference is given to using diethylene glycol monobutyl ether as the starter molecule.

Alkylene oxides suitable for the alkoxylation reaction include, in particular, ethylene oxide and propylene oxide, which can be used in any order or in a mixture in the alkoxylation reaction.

The polyalkylene oxide polyether alcohols are either straight polyethylene oxide polyethers or mixed polyalkylene oxide polyethers wherein at least 30 mole %, preferably at least 40 mole %, of the alkylene oxide units are ethylene oxide units. Preferred nonionic compounds are monofunctional mixed polyalkylene oxide polyethers which contain at least 40 mole % of ethylene oxide units and not more than 60 mole % of propylene oxide units.

Especially when using a hydrophilic agent containing ionic groups it is necessary to investigate its effect on the action of catalyst D). For this reason preference is given to nonionic compounds as hydrophilic agents.

Suitable catalyst compounds D) include, in addition to the ammonium or phosphonium salts of aliphatic carboxylic acids for use in accordance with the invention, the compounds known for catalyzing the reaction of isocyanate groups with isocyanate-reactive groups, individually or in mixtures with one another.

Examples include tertiary amines such as triethylamine, pyridine, methylpyridine, benzyldimethylamine, N,N-endoethylenepiperazine, N-methylpiperidine, penta-methyldiethylenetriamine, N,N-dimethylaminocyclohexane, N,N'-dimethylpiperazine or 1,4-diazabicyclo[2.2.2]octane (DABCO), or metal salts such as iron(III) chloride, tin(II) octoate, tin(II) ethylcaproate, tin(II) palmitate, dibutyltin(IV) dilaurate, dibutyltin(IV) diacetate and molybdenum glycolate or mixtures of such catalysts.

Suitable catalysts for use as component D) include tetrasubstituted ammonium or phosphonium salts of aliphatic or cycloaliphatic carboxylic acids, preferably those corresponding to formula (II),

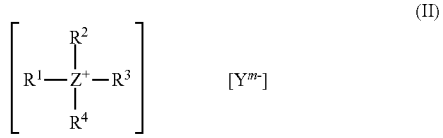

wherein
Z is nitrogen or phosphorus,
R¹, R², R³, R⁴ independently of one another are hydrogen or identical or different aliphatic, cycloaliphatic or araliphatic radicals having up to 24 carbon atoms and
Y is a carboxylate radical corresponding to formula (III),

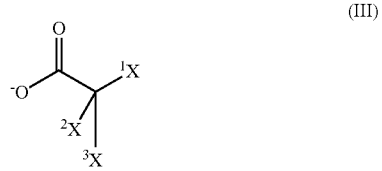

wherein
¹X, ²X, ³X independently of one another are substituents selected from hydrogen, halogen, cyano, hydroxyl, amide, ether, ester, thioether, ketone, aldehyde and carboxylate group and also aliphatic or cycloaliphatic radicals having up to 24 carbon atoms, which are optionally part of a cyclic or polycyclic system.

Preferred tetrasubstituted ammonium or phosphonium salts of aliphatic or cycloaliphatic carboxylic acids of formula (II) are tetraalkylammonium carboxylates which are preferably based on aliphatic carboxylic acids with branched alkyl radicals without additional functional groups.

Particularly preferred tetraalkylammonium carboxylates are tetrabutylammonium 2-ethylhexanoate, tetrabutylammonium pivalate, choline 2-ethylhexanoate, choline pivalate, methylcholine 2-ethylhexanoate and/or methylcholine pivalate, the preparation of which is described in U.S. Pat. No. 5,691,440.

In a preferred embodiment of the invention the preceding carboxylates are used as the sole compound of component D).

It is also possible to apply catalysts D) to support materials by methods known and to use them as heterogeneous catalysts.

The compounds of catalyst component D) can be dissolved advantageously in one of the components used in the process, or in a portion thereof. In particular, the carboxylates for use in accordance with the invention dissolve very well in the polar hydroxyalkyl acrylates, so that D) in solution in small amounts of B) can be metered in as a concentrated solution in liquid form.

In the process of the invention catalyst component D) is preferably used in amounts of 0.001 to 5.0% by weight, more preferably 0.01 to 2.0% by weight and most preferably 0.05 to 1.0% by weight, based on solids content of the product.

As component E) it is possible to use solvents or reactive diluents. Suitable solvents are inert towards the functional groups present in the product from the time of their addition until the end of the process. Suitable solvents include those used in the coating industry, such as hydrocarbons, ketones and esters, e.g. toluene, xylene, isooctane, acetone, butanone, methyl isobutyl ketone, ethyl acetate, butyl acetate, tetrahydrofuran, N-methylpyrrolidone, dimethylacetamide and dimethylformamide. It is preferred not to add any solvent.

As reactive diluents it is possible to use compounds which during UV curing are also (co)polymerized and hence incorporated into the polymer network and inert towards NCO groups. Such reactive diluents are described, by way of example, in P. K. T. Oldring (Ed.), Chemistry & Technology of UV & EB Formulations For Coatings, Inks & Paints, Vol. 2, 1991, SITA Technology, London, pp. 237-285. They may be esters of acrylic acid or methacrylic acid, preferably acrylic acid, with mono- or polyfunctional alcohols. Examples of suitable alcohols include the isomeric butanols, pentanols, hexanols, heptanols, octanols, nonanols and decanols; cycloaliphatic alcohols such as isobomol, cyclohexanol and alkylated cyclohexanols; dicyclopentanol; arylaliphatic alcohols such as phenoxyethanol and nonylphenylethanol; and tetrahydrofurfuryl alcohols. Additionally, it is possible to use alkoxylated derivatives of these alcohols.

Suitable dihydric alcohols include alcohols such as ethylene glycol, propane-1,2-diol, propane-1,3-diol, diethylene glycol, dipropylene glycol, the isomeric butanediols, neopentyl glycol, hexane-1,6-diol, 2-ethylhexanediol, tripropylene glycol or alkoxylated derivatives of these alcohols. Preferred dihydric alcohols are hexane-1,6-diol, dipropylene glycol and tripropylene glycol. Suitable trihydric alcohols include glycerol or trimethylolpropane or their alkoxylated derivatives. Tetrahydric alcohols include pentaerythritol or its alkoxylated derivatives.

The binders of the invention must be stabilized against premature polymerization. Therefore, as a constituent of component E), before and/or during the reaction, preferably phenolic stabilizers are added which inhibit the polymerization. Use is made in this context of phenols such as para-methoxyphenyl, 2,5-di-tert-butylhydroquinone or 2,6-di-tert-butyl-4-methylphenol. Also suitable are N-oxyl compounds for stabilization, such as 2,2,6,6-tetramethylpiperidine N-oxide (TEMPO) or its derivatives. The stabilizers can also be incorporated chemically into the binder; suitability in this context is possessed by compounds of the above-mentioned classes, especially if they still carry further free aliphatic alcohol groups or primary or secondary amine groups and thus can be attached chemically to compounds of component A) by way of urethane or urea groups. Particularly suitable for this purpose are 2,2,6,6-tetramethyl-4-hydroxypiperidine N-oxide. Preferred are phenolic stabilizers, especially para-methoxyphenol and/or 2,6-di-tert-butyl-4-methylphenol.

Other stabilizers, such as hindered amine light stabilizers (HALS), in contrast, are used less preferably in E), since they are known not to enable such effective stabilization and instead may lead to "creeping" free-radical polymerization of unsaturated groups.

In order to stabilize the reaction mixture, in particular the unsaturated groups, against premature polymerization it is possible to pass an oxygen-containing gas, preferably air, into and/or over the reaction mixture. It is preferred for the gas to have a very low moisture content in order to prevent unwanted reaction in the presence of isocyanate.

In general a stabilizer is added during the preparation of the binders of the invention, and at the end, in order to achieve a long-term stability, stabilization is repeated with a phenolic stabilizer, and optionally the reaction product is saturated with air.

In the process of the invention the stabilizer component is typically used in amounts of 0.001 to 5.0% by weight, preferably 0.01 to 2.0% by weight and more preferably 0.05 to 1.0% by weight, based on the solids content of the product.

The ratio of OH groups from component B) to the sum of NCO and uretdione groups from A) is preferably from 1.5:1.0 to 1.0:1.9, more preferably from 1.0:1.0 to 1.0:1.9 and most preferably from 1.0:1.0 to 1.0:1.2. The process of the invention is preferably carried out at temperatures of 20 to 130° C., more preferably of 40 to 100° C. and most preferably of 80 to 90° C.

Normally the NCO groups that may be present react more rapidly with the hydroxyl groups of component B) than do the uretdione groups of component A). Therefore, if two or more different constituents are present in B), it is possible to control the urethanization and allophanatization by means of the sequence of addition of the constituents such that one constituent of B) is preferably incorporated during the urethanization reaction, while the constituent added last is preferably incorporated during the allophanatization reaction.

The reaction of component A) with B) and further NCO-reactive compounds C) is over when all of the NCO groups, in accordance with the chosen stoichiometric proportions, have reacted with NCO-reactive groups from B) and C) and all uretdione groups, in accordance with the chosen stoichiometric proportions, have reacted with the hydroxyl groups from B). It is also possible to end the allophanatization by adding catalyst-deactivating compounds (for example, strong acids such as acidic phosphoric esters) or adding other isocyanate-containing compounds which scavenge the remaining compounds of component B).

It is immaterial whether the process of the invention is carried out continuously, for example, in a static mixer, extruder or compounder or batchwise, for example, in a stirred reactor. Preferably, the process of the invention is carried out in a stirred reactor, the sequence of addition of components A)-E) being arbitrary.

The course of the reaction can be monitored by means of suitable measuring instruments installed in the reaction vessel and/or on the basis of analyses on samples taken. Suitable techniques are known. They include viscosity measurements, measurements of the refractive index or the OH content, gas chromatography (GC), nuclear magnetic resonance spectroscopy (NMR), infrared spectroscopy (IR) and near infrared spectroscopy (NIR). Preference is given to using IR to check for any free NCO groups present (for aliphatic NCO groups, band at approximately $v=2272$ cm$^{-1}$) and, in particular, for uretdione groups (e.g. band for uretdiones based on hexamethylene diisocyanate at $v=1761$ cm$^{-1}$) and to GC analyses for unreacted compounds from B) and C).

In one preferred embodiment of the invention there is parallel allophanatization and urethanization of the compounds of component A). For that purpose A) is introduced initially, then stabilizers and, where appropriate, additives from E) are added, subsequently components B)-E) are added and the reaction mixture is brought to reaction temperature.

In another preferred embodiment initially A) is reacted with B) until the NCO groups have reacted completely. E) or parts thereof may already be present. Subsequently the reaction of the uretdione groups of A) with B) is initiated by adding D) and additionally, where appropriate, by adapting the temperature.

In one particularly preferred embodiment the isocyanate groups and the uretdione groups are reacted with an excess of hydroxyl groups of component B. The hydroxyl groups which remain following the reaction of A) with B), with catalysis of D), are subsequently reacted preferably with further isocyanate-containing compounds, in particular with those compounds described as component B), with urethanization.

The unsaturated allophanates obtained by the process of the invention preferably have viscosities measured using a cone-plate viscosimeter at 23° C. of ≤100 000 mPas, more preferably ≤75 000 mPas; preferably have number average molecular weights $M_n$ of from 600 to 3000 g/mol, more preferably from 750 to 1500 g/mol; and preferably contain less than 0.5% by weight of free di- and/or triisocyanate monomers, more preferably less than 0.1% by weight.

The binders of the invention can be used for producing coatings and paints and also adhesives, printing inks, casting resins, dental compounds, sizes, photoresists, stereolithography systems, resins for composite materials and sealants. In the case of adhesive bonding or sealing, it is a requirement, in the case of UV radiation curing, at least one of the two substrates to be bonded or sealed to one another is permeable to UV radiation, i.e, it must be transparent. In the case of electron beams, sufficient permeability for electrons should be ensured. Preferably, the binders are used in paints and coatings.

The coating compositions according to the invention contain
a) one or more of the binders obtained in accordance with the invention,
b) optionally one or more polyisocyanates containing free or blocked isocyanate groups, which are free from groups which react, with polymerization, with ethylenically unsaturated compounds on exposure to actinic radiation,
c) optionally compounds other than a), which contain groups which react, with polymerization, with ethylenically unsaturated compounds on exposure to actinic radiation, and optionally contain free or blocked NCO groups,
d) optionally one or more isocyanate-reactive compounds,
e) initiators, and
f) optionally solvents.

The polyisocyanates of component b), which are used in the coating compositions according to the invention, are known. Preferred are polyisocyanates which optionally contain isocyanurate, allophanate, biuret, uretdione and/or iminooxadiazinedione groups and are prepared from hexamethylene diisocyanate, isophorone diisocyanate, 4,4'-diisocyanatodicyclohexyhnethane and/or trimethylhexamethylene diisocyanate. The NCO groups may also blocked with the blocking agents previously described as suitable for blocking component A).

Compounds c) include urethane acrylates prepared from hexamethylene diisocyanate, isophorone diisocyanate, 4,4'-diisocyanatodicyclohexylmethane and/or trimethylhexamethylene diisocyanate, which may have been modified to contain isocyanurate, allophanate, biuret, uretdione and/or iminooxadiazinedione groups, and which do not contain isocyanate-reactive groups. NCO-containing urethane acrylates are available commercially from Bayer MaterialScience AG, Leverkusen, DE as Roskydal® UA VP LS 2337, Roskydal® UA VP LS 2396 or Roskydal® UA XP 2510.

Also suitable as component c) are the reactive diluents already described and known in the art of radiation-curing coatings, provided that they do not contain any NCO-reactive groups.

Compounds d) can be saturated or unsaturated and contain isocyanate-reactive groups, such as hydroxyl, amine or thiol. Preferred are saturated polyhydroxy compounds, such as polyether polyols, polyester polyols, polycarbonate polyols, poly(meth)acrylate polyols and/or polyurethane polyols which are known from the technology of coating, adhesive bonding, printing inks or sealants and which contain no groups which react, with polymerization, with ethylenically unsaturated compounds on exposure to actinic radiation.

Unsaturated hydroxy-functional compounds include the epoxy acrylates, polyester acrylates, polyether acrylates, urethane acrylates and acrylated polyacrylates which are known in the art of radiation-curing coatings and have an OH number of from 30 to 300 mg KOH/g. It is also possible to use the reactive diluents, previously described and known in the art of radiation-curing coatings, as a constituent of d), provided that they contain NCO-reactive groups.

Suitable initiators for free-radical polymerization, which can be used as component e), are those which can be activated thermally and/or by radiation. Photoinitiators, which are activated by UV or visible light, are preferred in this context. The photoinitiators are known compounds. A distinction is made between unimolecular (type I) and bimolecular (type II) initiators. Suitable (type I) systems include aromatic ketone compounds, e.g. benzophenones in combination with tertiary amines, alkylbenzophenones, 4,4'-bis(dimethylamino)benzophenone (Michler's ketone), anthrone and halogenated benzophenones or mixtures thereof. Suitable (type II) initiators include benzoin and its derivatives, benzil ketals, acylphosphine oxides, 2,4,6-trimethylbenzoyldiphenylphosphine oxide, bisacylphosphine oxides, phenylglyoxylic esters, camphorquinone, α-aminoalkylphenones, α,α-dialkoxyacetophenones and α-hydroxyalkylphenones.

The initiators are used in amounts of 0.1% to 10% by weight, preferably 0.1% to 5% by weight, based on the weight of the film-forming binder. The initiators can be used individually or, to obtain advantageous synergistic effects, in combination with one another.

When electron beams are used instead of UV irradiation there is no need for a photoinitiator. Electron beams are generated by means of thermal emission and accelerated by way of a potential difference. The high-energy electrons then pass through a titanium foil and are guided onto the binders to be cured. The general principles of electron beam curing are described in detail in "Chemistry & Technology of UV & EB Formulations for Coatings, Inks & Paints", Vol. 1, P. K. T Oldring (Ed.), SITA Technology, London, England, pp. 101-157, 1991.

Thermal curing of the activated double bonds can take place with the addition of thermally decomposing free-radical initiators. Suitable initiators include peroxy compounds such as dialkoxy dicarbonates, for example, bis(4-tert-butyl-cyclohexyl) peroxydicarbonate; dialkyl peroxides such as dilauryl peroxide; peresters of aromatic or aliphatic acids such as tert-butyl perbenzoate or tert-amyl peroxy 2-ethylhexanoate; inorganic peroxides such as ammonium peroxodisulphate or potassium peroxodisulphate; organic peroxides such as 2,2-bis(tert-butylperoxy)butane, dicumyl peroxide or tert-butyl hydroperoxide; and azo compounds such as 2,2'-azobis[N-(2-propenyl)-2-methylpropionamides], 1-[(cyano-1-methylethyl)azo]formamides, 2,2'-azobis(N-butyl-2-methylpropionamides), 2,2'-azobis(N-cyclohexyl-2-methylpropionamides), 2,2'-azobis{2-methyl-N-[2-(1-hydroxybutyl)]propionamides}, 2,2'-azobis {2-methyl-N-[2-(1-hydroxybutyl)]propionamides, or 2,2'-azobis{2-methyl-N-[1,1-bis(hydroxymethyl)-2-hydroxyethyl]propionamides. Also suitable are highly substituted 1,2-diphenylethanes (benzpinacols) such as 3,4-dimethyl-3,4-diphenylhexane, 1,1,2,2-tetraphenylethane-1,2-diol or the silylated derivatives thereof.

It is also possible to use a combination of initiators activable by UV light and thermally.

Additives e) include solvents of the type specified above under E). Additionally, it is possible for e), in order to increase the weather stability of the cured coating film, to contain UV absorbers and/or HALS stabilizers. Preferred is a combination of these stabilizers. The UV absorbers should have an absorption range of not more than 390 nm, such as the triphenyltriazine types (e.g. Tinuvin® 400 (Ciba Spezialitätenchemie GmbH, Lampertheim, DE)), benzotriazoles such as Tinuvin® 622 (Ciba Spezialitätenchemie GmbH, Lampertheim, DE) or oxalic dianilides (e.g. Sanduvor® 3206 (Clariant, Muttenz, CH))). They are added at 0.5% to 3.5% by weight, based on resin solids. Suitable HALS stabilizers are also available commercially and include (Tinuvin® 292 or Tinuvin® 123 (Ciba Spezialitätenchemie GmbH, Lampertheim, DE) or Sanduvor® 3258 (Clariant, Muttenz, CH). They are preferably added in amounts of 0.5% to 2.5% by weight based on resin solids.

It is also possible for component e) to contain pigments, dyes, fillers, levelling additives and devolatilizing additives.

Additionally it is possible, if necessary, for the catalysts known from polyurethane chemistry for accelerating the NCO/OH reaction to be present in e). They include tin salts, zinc salts, organotin compounds, tin soaps and/or zinc soaps such as tin octoate, dibutyltin dilaurate, dibutyltin oxide or tertiary amines such as diazabicyclo[2.2.2]octane (DABCO).

The application of the coating compositions of the invention to the material to be coated takes place using the methods known in coatings technology, such as spraying, knife coating, rolling, pouring, dipping, spin coating, brushing or squirting or by means of printing techniques such as screen, gravure, flexographic or offset printing and also by means of transfer methods.

Suitable substrates include wood, metal, including in particular metal as used in the applications of wire enamelling, coil coating, can coating or container coating, and also plastic, including plastic in the form of films, especially ABS, AMMA, ASA, CA, CAB, EP, UF, CF, MF, MPF, PF, PAN, PA, PE, HDPE, LDPE, LLDPE, UHMWPE, PET, PMMA, PP, PS, SB, PUR, PVC, RF, SAN, PBT, PPE, POM, PUR-RIM, SMC, BMC, PP-EPDM, and UP (abbreviations according to DIN 7728T1), paper, leather, textiles, felt, glass, wood, wood materials, cork, inorganically bonded substrates such as wooden boards and fiber cement slabs, electronic assemblies or mineral substrates. It is also possible to coat substrates containing a variety of the preceding materials, or to coat already coated substrates such as vehicles, aircraft or boats and also parts thereof, especially vehicle bodies or parts for exterior mounting. It is also possible to apply the coating compositions to a substrate temporarily, then to cure them partly or fully and optionally to detach them again, in order to produce films.

For curing it is possible to remove solvents present entirely or partly by flashing off. Subsequently or simultaneously it is possible for the optional thermal and the photochemical curing operation or operations to be carried out in succession or simultaneously. If necessary the thermal curing can take place at room temperature or at elevated temperature, preferably at 40 to 160° C., preferably at 60 to 130° C. and more preferably at 80 to 110° C.

Where photoinitiators are used in d) the radiation cure takes place preferably by exposure to high-energy radiation, in other words UV radiation or daylight, such as light having a wavelength 200 to 700 nm or by bombardment with high-energy electrons (electron beams, 150 to 300 keV). Radiation sources of light or UV light include high-pressure or medium-pressure mercury vapor lamps. It is possible for the mercury vapor to have been modified by doping with other elements such as gallium or iron. Lasers, pulsed lamps (known under the designation of UV flashlight lamps), halogen lamps or excimer emitters may also be used. As an inherent part of their design or through the use of special filters and/or reflectors, the emitters may be equipped so that part of the UV spectrum is prevented from being emitted. By way of example, for reasons of occupational hygiene, for example, the radiation assigned to UV-C or to UV-C and UV-B may be filtered out. The emitters may be installed in stationary fashion, so that the material for irradiation is conveyed past the radiation source by means of a mechanical device, or the emitters may be mobile and the material for irradiation may remain stationary during curing. The radiation dose which is normally sufficient for crosslinking in the case of UV curing is from 80 to 5000 mJ/cm$^2$.

Irradiation can also be carried out in the absence of oxygen, such as under an inert gas atmosphere or an oxygen-reduced atmosphere. Suitable inert gases are preferably nitrogen, carbon dioxide, noble gases or combustion gases. Irradiation may additionally take place by covering the coating with media transparent to the radiation. Examples include polymeric films, glass or liquids such as water.

Depending on the radiation dose and curing conditions it is possible to vary the type and concentration of any initiator used in known manner.

Particular preference is given to carrying out curing using high-pressure mercury lamps in stationary installations. Photoinitiators are then employed at concentrations of from 0.1% to 10% by weight, more preferably from 0.2% to 3.0% by weight, based on the solids content of the coating composition. For curing these coatings it is preferred to use a dose of from 200 to 3000 mJ/cm$^2$, measured in the wavelength range from 200 to 600 nm.

When thermally activable initiators are used in d), curing is carried out by increasing the temperature. The thermal energy may be introduced into the coating by means of radiation, thermal conduction and/or convection using ovens, near-infrared lamps and/or infrared lamps that are known in coatings technology.

The applied film thicknesses (prior to curing) are typically between 0.5 and 5000 µm, preferably between 5 and 1000 µm and more preferably between 15 and 200 µm. Where solvents are used, they are removed after application and before curing by known methods.

EXAMPLES

All percentages are by weight unless indicated otherwise.

The NCO contents in % were determined by back-titration with 0.1 mol/l hydrochloric acid following reaction with butylamine in accordance with DIN EN ISO 11909.

The viscosity measurements were carried out with a Viskolab LC3/ISO plate-and-cone viscometer (SM-KP) from Paar Physica, Ostfildern, DE in accordance with ISO/DIS 3219:1990.

Infrared spectroscopy was carried out on liquid films applied between sodium chloride plates in a model 157 instrument from Perkin Elmer, Überlingen, DE.

The content of residue monomers and volatile synthesis components were analyzed by means of GC (method using tetradecane as internal standard, oven temperature 110° C., injector temperature 150° C., carrier gas helium, instrument: 6890 N, Agilent, Waldbronn, DE, column: Restek RT 50, 30 m, 0.32 mm internal diameter, film thickness 0.25 µm).

The solids content was determined in accordance with DIN 53216/1 draft 4/89, ISO 3251.

An ambient temperature of 23° C., which prevailed at the time when the experiments were conducted is referred to as RT.

Desmodur® N 3400—HDI polyisocyanate predominantly containing uretdione groups, viscosity 185 mPa·s/23° C., NCO content 21.4%, commercial product of Bayer MaterialScience AG, Leverkusen, DE Desmorapid® Z—dibutyltin dilaurate (DBTL), commercial product of Bayer MaterialScience AG, Leverkusen, DE Darocur® 1173—photoinitiator, commercial product of Ciba Spezialitätenchemie GmbH, Lampertheim, DE Tone® M100—reaction product of 2 equivalents of ε-caprolactone with 1 equivalent of 2-hydroxyethyl acrylate, OH content 4.97%, viscosity 82 mPa·s/23° C., commercial product of Dow, Schwalbach, DE.

Example 1 describes the preparation of a suitable catalytically active carboxylate, which is employed in Example 2 for the reaction of compounds containing uretdione groups with ethylenically unsaturated hydroxyl compounds to give corresponding allophanate-containing compounds.

Example 1

Choline ethylhexanoate 272.13 g of a 40% solution of choline hydroxide and 145.73 g of 2-ethylhexanoic acid were stirred vigorously for 30 min at RT in a glass flask with reflux condenser, heatable oil bath, mechanical stirrer and internal thermometer. Water and methanol were distilled off in a rotary evaporator at 30-45° C. under a vacuum increased gradually to 20 mbar. The product was then taken up in n-hexane and re-evaporated in the rotary evaporator and dried at 0.1 mbar and 40° C. for 2 h, giving a slightly colored, viscous liquid whose $^1$H-NMR spectrum showed equimolar ratios of choline and ethylhexanoate, but only a weak signal in the region of aliphatic carboxylic acids.

Example 2

Allophanate-Containing Binder According to the Invention 263.47 g of Desmodur® N3400, 0.50 g of 2,6-di-tert-butyl-4-methylphenol and 0.07 g of Desmorapid® Z were introduced at RT into a three-necked flask with reflux condenser, stirrer, dropping funnel and air stream (0.5 l/h) and then heated to 60° C. 219.54 g of 2-hydroxyethyl acrylate were slowly added dropwise, during which a maximum temperature of 70° C. was reached. The reaction mixture was then held at 65° C. until the NCO content was <0.1%. A mixture of 14.43 g of 2-hydroxyethyl acrylate and 1.49 g of the catalyst from Example 1 was subsequently added dropwise. The reaction mixture was heated further and held at 80° C. until after 2.5 h only a very weak signal for uretdione groups was detected in the IR spectrum at ν=1768 cm$^{-1}$. 0.50 g of isophthaloyl dichloride were added, and the mixture was rapidly cooled to RT. Gas chromatography of a sample showed a hydroxyethyl acrylate content of 4.68%. 39.0 g of Desmodur N3400 and 0.07 g of Desmorapid® Z were added. The mixture was stirred at 60° C. until a signal for the isocyanate group was no longer present in the IR spectrum at ν=2272 cm$^{-1}$. Gas chromatography of a sample showed a hydroxyethyl acrylate content of 0.18%. A product having a viscosity of 64,500 mPas/23° C., an APHA color number of 104 and an NCO content of below 0.1% was obtained.

Comparison Example 3

Attempt to Prepare an Allophanate-Containing Binder

The catalysts described in US-A 2003/0153713 for the crosslinking of powder coating compositions containing uretdione group-containing curing agents and polymeric hydroxyl compounds without activated double bonds were examined for suitability.

Example 2 was repeated with the difference that, instead of the catalyst from Example 3, 0.51 g of tetrabutylammonium hydroxide was used as catalyst. The reaction mixture was heated to and held at 80° C. until after 2 h only a very weak signal for uretdione groups was detected in the IR spectrum at v=1768 cm$^{-1}$. 0.10 g of benzoyl chloride was added and the mixture was cooled rapidly to RT. During this cooling the reaction mixture turned cloudy. The hydroxyethyl acrylate content of a sample taken was found by gas chromatography to be 2.4%. 5.20 g of Desmodur® N3400 were added to the reaction mixture, which was stirred at 70° C. until in the IR spectrum at v=2272 cm$^{-1}$ there was no longer any signal for isocyanate groups. The hydroxyethyl acrylate content of a sample taken was found by gas chromatography to be 0.17%. A cloudy product was obtained with a viscosity of 84,000 mPas/23° C. and an NCO content of 0%.

Comparison Example 4

Attempt to Prepare an Allophanate-Containing Binder

The catalysts described in US-A 2003/0153713 for the crosslinking of powder coating compositions containing uretdione group-containing curing agents and polymeric hydroxyl compounds without activated double bonds were examined for suitability:

Example 2 was repeated with the difference that, instead of the catalyst from Example 3, 0.67 g of tetrabutylammonium fluoride was used as catalyst. The reaction mixture was heated to and held at 80° C. until after 3 h only a very weak signal for uretdione groups was detected in the IR spectrum at v=1768 cm$^{-1}$. 0.10 g of benzoyl chloride was added and the mixture was cooled rapidly to RT. During this cooling the reaction mixture turned cloudy, and a colorless precipitate formed. The hydroxyethyl acrylate content of a sample taken was found by gas chromatography to be 1.7%. 4.30 g of Desmodur® N3400 were added to the reaction mixture, which was stirred at 70° C. until in the IR spectrum at v=2272 cm$^{-1}$ there was no longer any signal for isocyanate groups. The hydroxyethyl acrylate content of a sample taken was found by gas chromatography to be 0.15%.

A cloudy product was obtained with a viscosity of 92,000 mPas/23° C. and an NCO content of 0%.

Comparison Examples 3 and 4 show that the catalysts which are suitable for crosslinking powder coating compositions containing uretdione group-containing curing agents and polymeric hydroxyl compounds are not suitable for the targeted synthesis of allophanates from uretdiones and alcohols. The resulting products are cloudy and have a relatively high viscosity making them unsuitable for producing coatings.

Example 5

Coating Formulation and Coating Material

A portion of the product from Example 2 was mixed thoroughly with 3.0% of the photoinitiator Darocur® 1173. Using a bone hand coater with a gap of 90 μm the mixture was drawn down in the form of a thin film onto a glass plate. UV irradiation (medium pressure mercury lamp, IST Metz GmbH, Nürtingen, DE, 750 mJ/cm$^2$) gave a hard, transparent coating which was solvent-resistant, had a pendulum hardness of 152 s, could hardly be damaged by scratching using steel wool (grade 0/0/0) in ten back-and-forth strokes with a force of 500 g directed onto the film and was not visibly altered after 100 back-and-forth strokes with a wad of cotton wool soaked in butyl acetate.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a radiation-curing binder containing allophanate groups which comprises reacting at a temperature of 40 to 100° C.,
   A) one or more compounds containing uretdione groups with
   B) one or more OH-functional compounds which contain groups which react, with polymerization, with ethylenically unsaturated compounds on exposure to actinic radiation,
   C) optionally NCO-reactive compounds other than B), in the presence of
   D) a catalyst selected from the group consisting of tetrabutylaminonium 2-ethylhexanoate, tetrabutylammonium pivalate, choline 2-ethylhexanoate, choline pivalate, methylcholine 2-ethylhexanoate and methylcholine pivalate,
to form allophanate groups by opening the uretdione ring.

2. The process of claim 1 wherein said compounds containing uretdione groups are prepared from hexamethylene diisocyanate.

3. The process of claim 1 wherein component B) comprises 2-hydroxyethyl acrylate and/or 4-hydroxybutyl acrylate.

4. The process of claim 2 wherein component B) comprises 2-hydroxyethyl acrylate and/or 4-hydroxybutyl acrylate.

5. A radiation-curing binder containing allophanate groups which is prepared by a process comprising reacting at a temperature of 40 to 100° C.,
   A) one or more compounds containing uretdione groups with
   B) one or more OH-functional compounds which contain groups which react, with polymerization, with ethylenically unsaturated compounds on exposure to actinic radiation,
   C) optionally NCO-reactive compounds other than B), in the presence of
   D) a catalyst selected from the group consisting of tetrabutylammonium 2-ethylhexanoate, tetrabutylammonium pivalate, choline 2-ethylhexanoate, choline pivalate, methylcholine 2-ethylhexanoate and methylcholine pivalate,
to form allophanate groups by opening the uretdione ring.

6. The radiation-curing binder of claim 5 wherein said compounds containing uretdione groups are prepared from hexamethylene diisocyanate.

7. The radiation-curing binder of claim 5 wherein component B) comprises 2-hydroxyethyl acrylate and/or 4-hydroxybutyl acrylate.

8. The radiation-curing binder of claim 6 wherein component B) comprises 2-hydroxyethyl acrylate and/or 4-hydroxybutyl acrylate.

9. A coating composition comprising
   a) one or more of the radiation-curing binders containing allophanate groups of claim 5,
   b) optionally one or more polyisocyanates containing free or blocked isocyanate groups, which are free from groups which react, with polymerization, with ethylenically unsaturated compounds on exposure to actinic radiation,
c) optionally compounds other than a), which contain groups which react, with polymerization, with ethylenically unsaturated compounds on exposure to actinic radiation, and optionally contain free or blocked NCO groups,
d) optionally one or more isocyanate-reactive compounds,
e) one or more initiators, and
f) optionally solvents.

10. A substrate coated with a coating obtained from the radiation-curing binder containing allophanate groups of claim 5.

11. A process for preparing a radiation-curing binder containing allophanate groups, wherein the radiation-curing binder has a number average molecular weight from 600 to 1500 g/mol, which comprises reacting at a temperature of 40 to 100° C.
A) one or more compounds containing uretdione groups with
B) one or more OH functional compounds which contain groups which react, with polymerization, with ethylenically unsaturated compounds on exposure to actinic radiation,
C) optionally NCO reactive compounds other than B), in the presence of
D) a catalyst selected from the group consisting of tetrabutylammonium 2-ethylhexanoate, tetrabutylammonium pivalate, choline 2-ethylhexanoate, choline pivalate, methylcholine 2-ethylhexanoate and methylcholine pivalate,
to form allophanate groups by opening the uretdione ring.

12. A radiation curing binder containing allophanate groups, wherein the radiation-curing binder has a number average molecular weight from 600 to 1500 g/mol, which is prepared by a process comprising reacting at a temperature of 40 to 100° C.
A) one or more compounds containing uretdione groups with
B) one or more OH functional compounds which contain groups which react, with polymerization, with ethylenically unsaturated compounds on exposure to actinic radiation,
C) optionally NCO reactive compounds other than B), in the presence of
D) a catalyst selected from the group consisting of tetrabutylammonium 2-ethylhexanoate, tetrabutylammonium pivalate, choline 2-ethylhexanoate, choline pivalate, methylcholine 2-ethylhexanoate and methylcholine pivalate,
to form allophanate groups by opening the uretdione ring.

13. The process of claim 11, wherein the radiation-curing binder has a number average molecular weight of from 750 to 1500 g/mol.

14. The radiation curing binder of claim 12, wherein the radiation-curing binder has a number average molecular weight of from 750 to 1500 g/mol.

15. A process for preparing a radiation-curing binder containing allophanate groups which comprises reacting at a temperature of 40 to 100° C.
A) one or more compounds containing uretdione groups with
B) one or more OH functional compounds which contain groups which react, with polymerization, with ethylenically unsaturated compounds on exposure to actinic radiation,
C) optionally NCO reactive compounds other than B), in the presence of
D) a catalyst comprising choline 2-ethylhexanoate,
to form allophanate groups by opening the uretdione ring.

16. A radiation-curing binder containing allophanate groups which is prepared by a process comprising reacting at a temperature of 40 to 100° C.
A) one or more compounds containing uretdione groups with
B) one or more OH functional compounds which contain groups which react, with polymerization, with ethylenically unsaturated compounds on exposure to actinic radiation,
C) optionally NCO reactive compounds other than B), in the presence of
D) a catalyst comprising choline 2-ethylhexanoate,
to form allophanate groups by opening the uretdione ring.

* * * * *